US012612856B2

(12) United States Patent
Yuan et al.

(10) Patent No.: US 12,612,856 B2
(45) Date of Patent: Apr. 28, 2026

(54) LOST CIRCULATION DETECTION DEVICE

(71) Applicants:PetroChina Company Limited, Beijing (CN); CNPC Engineering Technology R&D Company Limited, Beijing (CN)

(72) Inventors: Guangjie Yuan, Beijing (CN); Jingcui Li, Beijing (CN); Yan Xia, Beijing (CN); Jifang Wan, Beijing (CN); Gentai Jin, Beijing (CN); Guotao Li, Beijing (CN); Hong Zhang, Beijing (CN); Tianen Liu, Beijing (CN); Pan Fu, Beijing (CN); Yuhan Pang, Beijing (CN)

(73) Assignees: PetroChina Company Limited, Beijing (CN); CNPC Engineering Technology R&D Company Limited, Beijing (CN)

( * ) Notice: Subject to any disclaimer, the term of this patent is extended or adjusted under 35 U.S.C. 154(b) by 380 days.

(21) Appl. No.: 18/521,195

(22) Filed: Nov. 28, 2023

(65) Prior Publication Data

US 2024/0093599 A1     Mar. 21, 2024

Related U.S. Application Data

(63) Continuation of application No. PCT/CN2022/126525, filed on Oct. 20, 2022.

(30) Foreign Application Priority Data

Mar. 31, 2022   (CN) ......................... 202210336295.4

(51) Int. Cl.
| | |
|---|---|
| *E21B 47/10* | (2012.01) |
| *E21B 21/08* | (2006.01) |
| *G01N 33/28* | (2006.01) |

(52) U.S. Cl.
CPC .............. *E21B 47/10* (2013.01); *E21B 21/08* (2013.01); *G01N 33/2823* (2013.01)

(58) Field of Classification Search
CPC ...... E21B 47/10; E21B 21/08; G01N 33/2823
See application file for complete search history.

(56) References Cited

U.S. PATENT DOCUMENTS

| | | | |
|---|---|---|---|
| 4,034,218 | A | 7/1977 | Turcotte |
| 4,492,865 | A | 1/1985 | Murphy et al. |
| | | (Continued) | |

FOREIGN PATENT DOCUMENTS

| | | | |
|---|---|---|---|
| CN | 2760228 | Y | 2/2006 |
| CN | 203022732 | U | 6/2013 |
| | | (Continued) | |

OTHER PUBLICATIONS

Office Action from corresponding Chinese Application No. 202210336295.4 mailed on Jul. 20, 2024, 16 pages with translation.

(Continued)

*Primary Examiner* — Jill E Culler
(74) *Attorney, Agent, or Firm* — Tucker Ellis LLP

(57) ABSTRACT

A lost circulation detection device includes a first detection member and a second detection member, a first signal transmitter and a first signal receiver are disposed on the first detection member, and the first signal transmitter transmits a signal along an axial direction of a rockshaft so that the first signal receiver acquires data information of drilling fluid in the axial direction of the rockshaft; a fluid channel penetrating through the second detection member is disposed in the second detection member, and the fluid channel is configurable to be in communication with the rockshaft; a second signal transmitter and a second signal receiver are disposed oppositely on two sides of the fluid channel, and the second signal transmitter transmits a signal along a (Continued)

center line of a second accommodating groove, so that the second signal receiver acquires data information of drilling fluid in a circumferential direction of the rockshaft.

20 Claims, 5 Drawing Sheets

(56) References Cited

U.S. PATENT DOCUMENTS

| | | | |
|---|---|---|---|
| 10,655,455 B2 * | 5/2020 | Hopper | .................. E21B 21/08 |
| 2017/0030884 A1 * | 2/2017 | Sreekumar | ........... G01N 21/643 |
| 2018/0080317 A1 * | 3/2018 | Hopper | .................. E21B 21/08 |
| 2018/0128937 A1 | 5/2018 | Donzier et al. | |

FOREIGN PATENT DOCUMENTS

| | | |
|---|---|---|
| CN | 205370560 U | 7/2016 |
| CN | 207568595 U | 7/2018 |
| CN | 111364978 A | 7/2020 |
| CN | 112228047 A | 1/2021 |
| CN | 113586036 A | 11/2021 |
| CN | 114704249 A | 7/2022 |
| CN | 114876448 A | 8/2022 |
| JP | 2001-303611 A | 10/2001 |
| RU | 2374441 C2 | 11/2009 |
| RU | 2495241 C2 | 10/2013 |
| RU | 2558556 C1 | 8/2015 |
| SU | 945399 A1 | 7/1982 |
| SU | 1498914 A2 | 8/1989 |
| WO | 2023184941 A1 | 10/2023 |

OTHER PUBLICATIONS

Notice of Allowance from corresponding Russian Application No. 2023134309/03 mailed on May 24, 2024, 23 pages with translation.
International Search Report and Written Opinion of corresponding International Application No. PCT/CN2022/126525, dated Nov. 29, 2022, 16 pages.

* cited by examiner

LOST CIRCULATION DETECTION DEVICE

CROSS-REFERENCE TO RELATED APPLICATIONS

This application is a continuation of International Application No. PCT/CN2022/126525, filed on Oct. 20, 2022, which claims priority to Chinese Patent Application No. 202210336295.4, filed with China National Intellectual Property Administration on Mar. 31, 2022, and entitled "LOST CIRCULATION DETECTION DEVICE". The disclosures of the aforementioned applications are hereby incorporated by reference in their entireties.

TECHNICAL FIELD

The embodiments of the present disclosure relate to the technical field of petroleum exploration and, in particular, to a lost circulation detection device.

BACKGROUND

During drilling construction, lost circulation is an abnormal working condition that is often encountered. For example, when there are certain fractures and voids in the formation around a drilling borehole, drilling fluid may be lost to the surrounding fractures and voids, which will lead to occurrence of lost circulation. The occurrence of lost circulation may waste a lot of drilling fluid and effective drilling time, and even lead to borehole scrapping, resulting in huge economic losses. Therefore, it is necessary to find the leakage point in time and accurately and stop the leakage.

In order to solve the above technical problems, a lost circulation detector is usually used to detect the leakage point. The lost circulation detector in the related technology is usually provided with a sensor, which may collect relevant data of drilling fluid in a rockshaft along an axial direction of the rockshaft, such as a flow velocity, temperature and pressure of the drilling fluid, so that a corresponding leakage point is found by analyzing the collected data.

However, the above-described lost circulation detector has a great detection error, which leads to the inability to accurately determine the position of the leakage point, and further affects the efficiency of drilling and increases the cost of drilling.

SUMMARY

The embodiments of the present disclosure provide a lost circulation detection device for solving the technical problem that a lost circulation detection device in the related art cannot accurately determine a position of a leakage point.

The solution of an embodiment of the present disclosure to solve the above technical problem is as follows:

a lost circulation detection device including:

a first detection member, where a first accommodating groove is disposed on a side wall of the first detection member, and the first accommodating groove is configurable to be in communication with a rockshaft; a first signal transmitter and a first signal receiver are disposed in the first accommodating groove, and the first signal transmitter and the first signal receiver are disposed oppositely and spaced apart along an axial direction of the rockshaft, and the first signal transmitter transmits a signal along the axial direction of the rockshaft, so that the first signal receiver acquires data information of drilling fluid in the axial direction of the rockshaft; and a second detection member securely connected with the first detection member; where a fluid channel penetrating through the second detection member is disposed in the second detection member, and the fluid channel is configurable to be in communication with the rockshaft; a second accommodating groove is further disposed in the second detection member, and the second accommodating groove penetrates through the fluid channel and intersects with a center line of the fluid channel; a second signal transmitter and a second signal receiver are disposed in the second accommodating groove, and the second signal transmitter and the second signal receiver are disposed oppositely on two sides of the fluid channel, and the second signal transmitter transmits a signal along a center line of the second accommodating groove, so that the second signal receiver acquires data information of drilling fluid in a circumferential direction of the rockshaft.

The embodiments of the present disclosure have the following beneficial effects: the embodiments of the present disclosure provide a lost circulation detection device including a first detection member and a second detection member, where a first signal transmitter and a first signal receiver are correspondingly disposed on the first detection member, and when the lost circulation detection device moves up and down along an axial direction of a rockshaft, data information of drilling fluid can be collected along the axial direction of the rockshaft through the first signal transmitter and the first signal receiver; meanwhile, a fluid channel penetrating through the second detection member is disposed in the second detection member, and the fluid channel is in communication with the rockshaft, so that drilling fluid can flow into the fluid channel; a second signal transmitter and a second signal receiver are disposed on the second detection member, and the second signal transmitter and the second signal receiver are disposed oppositely on two sides of the fluid channel, so that a signal transmitted by the second signal transmitter penetrates through drilling fluid in the fluid channel and is received by the second signal receiver, thereby realizing the collection of data of drilling fluid in the circumferential direction in the fluid channel, that is, equivalent to realizing the collection of data information of drilling fluid in the circumferential direction of the rockshaft. Based on the above description, when positions of the leakage detected by the first detection member and the second detection member are in the same range, it indicates that the position of the leakage point is relatively accurate; when the positions of the leakage detected by the first detection member and the second detection member are in different ranges, it indicates that there is an error in the collected data, so that the staff can be reminded to find the problem in time and make corresponding adjustments. Therefore, by using the above two detection members for mutual calibration of the position of a leakage, the detection result is more accurate and the positioning accuracy is higher.

On the basis of the above technical solution, the following improvement can be made to the embodiments of the present disclosure.

In a possible implementation, a first mounting seat is disposed in the first accommodating groove, and a first mounting cavity and a second mounting cavity are disposed oppositely and spaced apart on the first mounting seat along the axial direction of the rockshaft, and the first signal transmitter is disposed in the first mounting cavity, and the first signal receiver is disposed in the second mounting cavity, and a transmitting end of the first signal transmitter is disposed oppositely to and collinear with a receiving end of the first signal receiver.

In a possible implementation, the first signal transmitter includes a first signal transmitting probe and a first signal transmitting sleeve, the first signal transmitting probe is disposed in the first signal transmitting sleeve; the first signal transmitting sleeve is slidably disposed in the first mounting cavity, and a first magnet is disposed at an end of the first signal transmitting sleeve near a top of the first mounting cavity; and a first electromagnet is disposed at the top of the first mounting cavity, and the first electromagnet is disposed oppositely to the first magnet; and along the axial direction of the rockshaft, there is a certain space between the first electromagnet and the first signal transmitting sleeve.

In a possible implementation, the second signal transmitter includes a second signal transmitting probe and a second signal transmitting sleeve, and the second signal transmitting probe is disposed in the second signal transmitting sleeve; the second signal transmitting sleeve is slidably disposed in the second accommodating groove, and a second magnet is disposed at an end of the second signal transmitting sleeve near a top of the second accommodating groove; and a second electromagnet is disposed at the top of the second accommodating groove, and the second electromagnet is disposed oppositely to the second magnet; and in a direction along the center line of the second accommodating groove, there is a certain space between the second electromagnet and the second signal transmitting sleeve.

In a possible implementation, an angle between the center line of the second accommodating groove and the center line of the fluid channel is 20°-60°.

In a possible implementation, the first detection member is provided with a first accommodating cavity and a first sealing plate, and the first sealing plate seals an opening of the first accommodating cavity; and a first circuit board is disposed in the first accommodating cavity, and the first circuit board is electrically connected with the first signal transmitter and the first signal receiver, respectively; and the second detection member is provided with a second accommodating cavity and a second sealing plate, and the second sealing plate seals an opening of the second accommodating cavity; a second circuit board is disposed in the second accommodating cavity, and the second circuit board is electrically connected with the second signal transmitter and the second signal receiver, respectively.

In a possible implementation, a first temperature detector and a first pressure detector are disposed on the side wall of the first detection member, and both the first temperature detector and the first pressure detector are electrically connected with the first circuit board; and a second temperature detector and a second pressure detector are disposed on a side wall of the second detection member, and both the second temperature detector and the second pressure detector are electrically connected with the second circuit board.

In a possible implementation, the first detection member and the second detection member are disposed along the axial direction of the rockshaft, and a telescopic device is disposed between the first detection member and the second detection member, and a telescopic direction of the telescopic device is parallel to the axial direction of the rockshaft; and the telescopic device is connected, at one end, with the first detection member, and the telescopic device is connected, at the other end, with the second detection member through a first centralizer, and the first centralizer is provided with a liquid inlet hole which is configurable to be in communication with the rockshaft and the fluid channel respectively.

In a possible implementation, the telescopic device includes:

a cylinder body firmly connected with the first detection member;

a piston slidably disposed in the cylinder body, where an outer side wall of the piston fits an inner side wall of the cylinder body; and a telescopic rod, one end of which is firmly connected with the piston, and the other end of which is connected with the second detection member.

In a possible implementation, a protector for protecting the second detection member is disposed at a bottom of the second detection member.

BRIEF DESCRIPTION OF DRAWINGS

In order to more clearly explain technical solutions in embodiments of the present disclosure or the related technology, the drawings needed to be used in the description of the embodiments or the related technology will be briefly introduced below. Obviously, the drawings in the following description are intended for only some embodiments of the present disclosure, and other drawings may be obtained according to the structures shown in these drawings without creative labor for those ordinarily skilled in the art.

Figure 1:
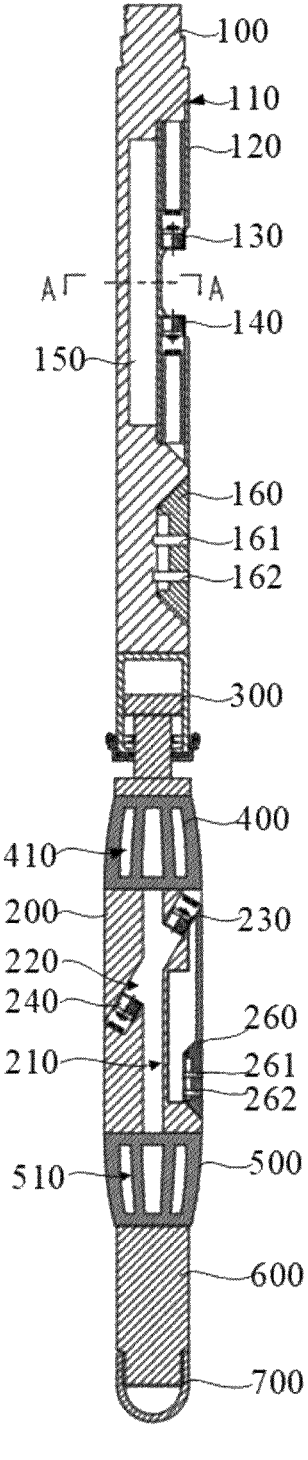
FIG. 1 is an overall structural schematic diagram of a lost circulation detection device provided in an embodiment of the present disclosure.

In the drawings, components represented by reference numerals are listed as follows:

100: first detection member;

110: first accommodating groove;

120: first mounting seat; 121: first mounting cavity; 122: second mounting cavity; 123: first plate body; 124:

second plate body; 125: third plate body; 126: fourth plate body; 127: first electromagnet; 128: third electromagnet;

130: first signal transmitter; 131: first signal transmitting probe; 132: first signal transmitting sleeve; 133: first magnet;

140: first signal receiver; 141: first signal receiving probe; 142: first signal receiving sleeve; 143: third magnet;

150: first accommodating cavity;

160: second mounting seat; 161: first temperature detector; 162: first pressure detector;

200: second detection member;

210: fluid channel;

220: second accommodating groove; 221: first accommodating sub-groove; 222: second electromagnet; 223: second accommodating sub-groove; 224: fourth electromagnet;

230: second signal transmitter; 231: second signal transmitting probe; 232: second signal transmitting sleeve; 233: second magnet;

240: second signal receiver; 241: second signal receiving probe; 242: second signal receiving sleeve; 243: fourth magnet;

250: second accommodating cavity;

260: third mounting seat; 261: second temperature detector; 262: second pressure detector;

300: telescopic device;

310: cylinder body; 320: piston; 330: telescopic rod; 340: first sealing gasket; 350: first limit plate; 360: second sealing gasket; 370: second limit plate; 380: fixing plate; 381: securing bolt; 390: fixing block;

400: first centralizer; 410: liquid inlet hole;

500: second centralizer; 510: liquid outlet hole;

600: connector;

700: protective cover.

DESCRIPTION OF EMBODIMENTS

During drilling construction, lost circulation is an abnormal working condition that is often encountered. For example, when there are certain fractures and voids in the formation around a drilling borehole, drilling fluid may be lost to the surrounding fractures and voids, which will lead to occurrence of lost circulation. The occurrence of lost circulation may waste a lot of drilling fluid and effective drilling time, and even lead to borehole scrapping, resulting in huge economic losses. Therefore, it is necessary to find the leakage point in time and accurately and stop the leakage.

In order to solve the above technical problems, a lost circulation detector is usually used to detect the leakage point. The lost circulation detector in the related technology is usually provided with a sensor, which may collect relevant data of drilling fluid in a rockshaft along an axial direction of the rockshaft, such as a flow velocity, temperature and pressure of the drilling fluid, so that a corresponding leakage point is found by analyzing the collected data. However, the above-described lost circulation detector can only collect the relevant data of drilling fluid along the axial direction of the rockshaft through the sensor, but this data cannot be verified. Therefore, when the sensor fails or its sensitivity decreases, the data it collects will present a big error which cannot be found by the staff in time, thereby leading to inability to determine the position of a leakage point in time and accurately, and further affecting the drilling efficiency and increasing the drilling cost.

In view of this, the embodiments of the present disclosure provide a lost circulation detection device including a first detection member and a second detection member, where a first signal transmitter and a first signal receiver are oppositely disposed on the first detection member along an axial direction of a rockshaft, so that the first detection member may collect data information of drilling fluid along the axial direction of the rockshaft; meanwhile, a fluid channel penetrating through the second detection member is disposed in the second detection member, and the fluid channel is in communication with the rockshaft, so that drilling fluid can flow into the fluid channel; and a second signal transmitter and a second signal receiver are oppositely disposed on two sides of the fluid channel, so that the second detection member can collect data information of drilling fluid along a circumferential direction of the rockshaft. Based on the above description, when positions of the leakage detected by the first detection member and the second detection member are in the same range, it indicates that the position of the leakage point is relatively accurate; when the positions of the leakage detected by the first detection member and the second detection member are in different ranges, it indicates that there is an error in the collected data, so that the staff can be reminded to find the problem in time and make corresponding adjustments. Therefore, by using the above two detection members for mutual calibration of the position of a leakage, the detection result is more accurate and the positioning accuracy is higher.

In order to make the above objectives, features and advantages of the embodiments of the present disclosure more obvious and understandable, the technical solutions in the embodiments of the present disclosure will be described clearly and comprehensively in conjunction with the drawings. Obviously, the described embodiments are only some but not all of the embodiments of the present disclosure. Based on the embodiments in the present disclosure, all other embodiments obtained by those ordinarily skilled in the art without creative labor fall within the protection scope of the present disclosure.

Referring to FIG. 1, an embodiment of the present disclosure provides a lost circulation detection device, which includes a first detection member 100 and a second detection member 200; and one end of the first detection member 100 is securely connected with one end of the second detection member 200. The first detection member 100 is provided with a first signal detector, which may be used to collect data information of drilling fluid along an axial direction of a rockshaft; and the second detection member 200 is provided with a second signal detector, which may be used to collect data information of drilling fluid along a circumferential direction of the rockshaft.

A first accommodating groove 110 may be disposed on a side wall of the first detection member 100, and the first accommodating groove 110 is configurable to be in communication with the rockshaft, so that drilling fluid can flow into the first accommodating groove 110. Meanwhile, a first signal detector is disposed in the first accommodating groove 110, the first signal detector includes a first signal transmitter 130 and a first signal receiver 140, and the first signal transmitter 130 and the first signal receiver 140 are disposed oppositely and spaced apart along the axial direction of the rockshaft, that is, a transmitting end of the first signal transmitter 130 and a receiving end of the first signal receiver 140 are disposed oppositely, so that the first signal transmitter 130 can transmit a signal along the axial direction of the rockshaft, and the first signal receiver 140 can acquire data information of drilling fluid in the axial direction of the rockshaft. Meanwhile, there is a certain space between the first signal transmitter 130 and the first signal receiver 140 along the axial direction of the rockshaft, and drilling fluid may flow into this space, so that the first detection member 100 can collect data information of drilling fluid at this space section. Therefore, as the lost circulation detection device moves up and down along the axial direction of the rockshaft, the first detection member 100 may collect all data information of drilling fluid along the axial direction of the rockshaft, thereby completing the detection of the position of the leakage in the axial direction of the rockshaft.

Exemplarily, the first detection member 100 may be in a columnar shape, and a first accommodating groove 110 is disposed on a side wall thereof, and the first accommodating groove 110 may be in an arc shape. An opening of the first accommodating groove 110 faces an inner wall of the rockshaft, and a length direction of the first accommodating groove 110 is parallel to the axial direction of the rockshaft. A first mounting seat 120 may be disposed in the first accommodating groove 110, and a length direction of the first mounting seat 120 is consistent with the length direction of the first accommodating groove 110, and the first mounting seat 120 may be disposed in the first accommodating groove 110 by welding. And along the axial direction of the rockshaft, a first mounting cavity 121 and a second mounting cavity 122 are disposed oppositely and spaced apart on the first mounting seat 120; a first signal transmitter 130 is disposed in the first mounting cavity 121, a first signal receiver 140 is disposed in the second mounting cavity 122, and a transmitting end of the first signal transmitter 130 is disposed oppositely to and collinear with a receiving end of the first signal receiver 140.

Figure 2:
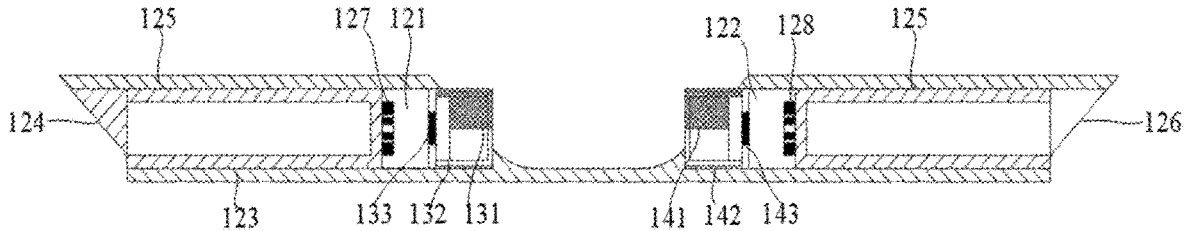
FIG. 2 is a structural schematic diagram of a first mounting seat of a lost circulation detection device provided in an embodiment of the present disclosure.
Figure 3:
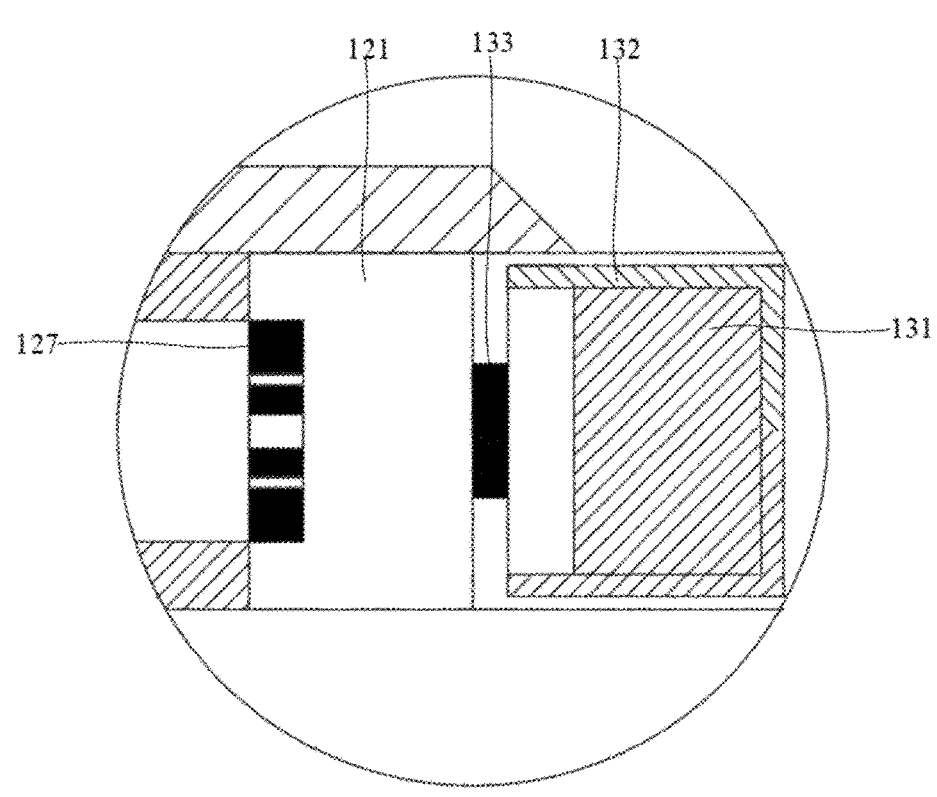
FIG. 3 is a partial structural schematic diagram I of a lost circulation detection device provided in an embodiment of the present disclosure.
Figure 4:
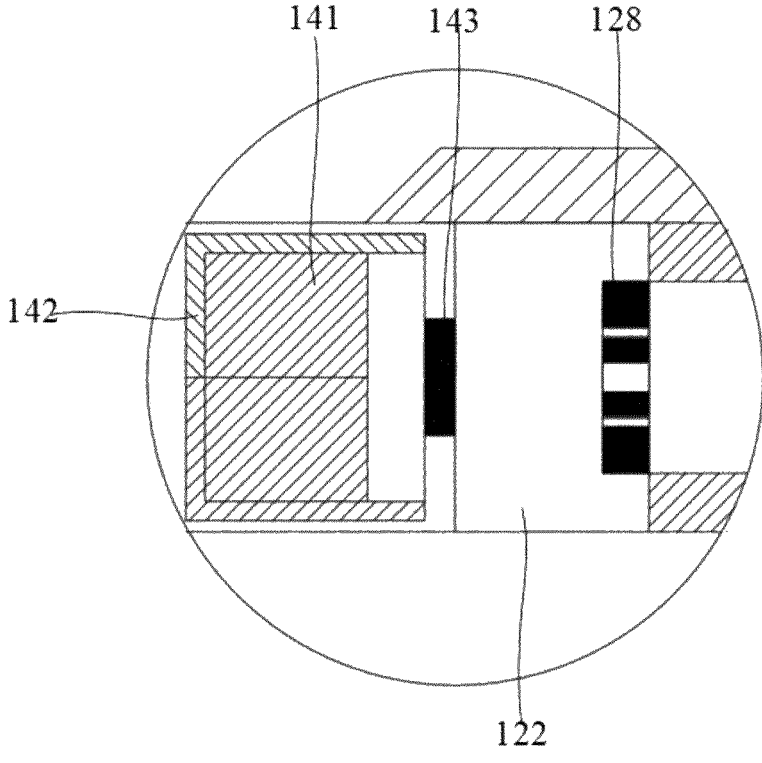
FIG. 4 is a partial structural schematic diagram II of a lost circulation detection device provided in an embodiment of the present disclosure.
Figure 5:
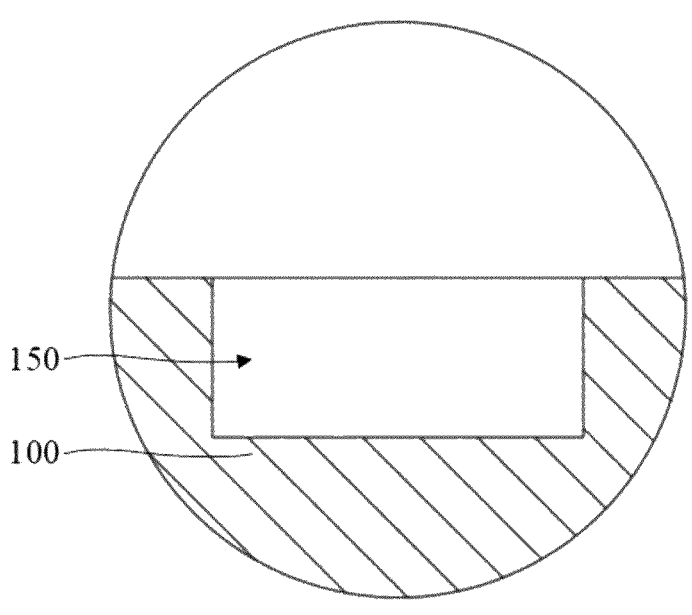
FIG. 5 is a partial cross-sectional view along a direction A-A of a lost circulation detection device provided in an embodiment of the present disclosure.

As shown in FIG. 2 to FIG. 4, the first mounting seat 120 may include a first plate body 123, a second plate body 124, a third plate body 125 and a fourth plate body 126 which are connected in sequence. The first plate body 123 and the third plate body 125 are disposed oppositely and spaced apart, that is, there is a cavity between the first plate body 123 and the third plate body 125, and the first plate body 123 and the third plate body 125 extend along the axial direction of the rockshaft, that is, the first plate body 123 and the third plate body 125 both extend from a top of the first accommodating groove 110 to a bottom of the first accommodating groove 110, and upper edges and lower edges of the first plate body 123 and the third plate body 125 may be curved, so that the first plate body 123 and the third plate body 125 can fit an inner wall of the first accommodating groove 110. Meanwhile, the second plate body 124 and the fourth plate body 126 are disposed oppositely, that is, the second plate body 124 and the fourth plate body 126 are located at the top and the bottom of the first mounting seat 120, respectively, and the second plate body 124 and the fourth plate body 126 may also be in an arc structure, so that the second plate body 124 and the fourth plate body 126 can fit the inner wall of the first accommodating groove 110. Therefore, the first mounting seat 120 with a cavity structure is surrounded by the first plate body 123, the second plate body 124, the third plate body 125 and the fourth plate body 126, and this cavity includes the first mounting cavity 121 and the second mounting cavity 122 which are spaced apart.

Further, the third plate body 125 may include a first sub-plate and a second sub-plate spaced apart along the axial direction of the rockshaft.

A top end of the first sub-plate is connected with the second plate body 124, and a bottom end of the first sub-plate extends along the axial direction of the rockshaft;

and there is a cavity between the first sub-plate and the first plate body 123, which forms a first mounting cavity 121; and a bottom of the first mounting cavity 121 may be an opening. Meanwhile, a first reinforcing frame may be disposed in the first mounting cavity 121, which is connected with the first plate body 123, the second plate body 124 and the first sub-plate respectively; and by disposing the reinforcing frame, the first mounting cavity 121 may be supported, thereby preventing the first mounting cavity 121 from being deformed under the impact of drilling fluid. In addition, there is a certain space between a bottom of the first reinforcement frame and the opening of the first mounting cavity 121, and the first signal transmitter 130 is disposed in this space, and the transmitting end of the first signal transmitter 130 is located at the opening of the first mounting cavity 121, so that the transmitting end of the first signal transmitter 130 can be in contact with drilling fluid.

The second sub-plate is located below the first sub-plate, and there is a certain space between a top end of the second sub-plate and a bottom end of the first sub-plate. A bottom end of the second sub-plate is connected with the fourth plate body 126, and the top end of the second sub-plate extends towards the first sub-plate along the axial direction of the rockshaft; and there is a cavity between the second sub-plate and the first plate body 123, which forms a second mounting cavity 122, and a top of the second mounting cavity 122 may be an opening. Meanwhile, a second reinforcing frame is disposed in the second mounting cavity 122, which is connected with the first plate body 123, the fourth plate body 126 and the second sub-plate respectively; and by disposing the second reinforcing frame, the second mounting cavity 122 can be supported, thereby preventing the second mounting cavity 122 from being deformed under the impact of drilling fluid. In addition, there is a certain space between a top of the second reinforcement frame and the opening of the second mounting cavity 122, and the first signal receiver 140 is disposed at the space, and the receiving end of the first signal receiver 140 is located at the opening of the second mounting cavity 122, so that the receiving end of the first signal receiver 140 can be in contact with drilling fluid. Therefore, by adopting the above structure, drilling fluid can flow to the space between the first mounting cavity 121 and the second mounting cavity 122, so that the drilling fluid is in contact with the first signal transmitter 130 and the first signal receiver 140, thereby achieving the collection, by the first detection member 100, of information of drilling fluid in the axial direction of the rockshaft.

In addition, a first electromagnet 127 is disposed at a top of the first mounting cavity 121, in other words, the first electromagnet 127 is disposed on a bottom end surface of the first reinforcing frame. A third electromagnet 128 is disposed at a bottom of the second mounting cavity 122, in other words, the third electromagnet 128 is disposed on a top end surface of the second reinforcing frame.

Exemplarily, the first signal transmitter 130 may include a first signal transmitting probe 131 and a first signal transmitting sleeve 132. The first signal transmitting probe 131 is disposed in the first signal transmitting sleeve 132, and the first signal transmitting probe 131 may extend to the outside of the first signal transmitting sleeve 132, so that it is more convenient to collect data information of drilling fluid. The first signal transmitting sleeve 132 is slidably disposed in the first mounting cavity 121, and a first magnet 133 is disposed at an end of the first signal transmitting sleeve 132 near the top of the first mounting cavity 121, the first magnet 133 is disposed oppositely to the first electromagnet 127, meanwhile, there is a certain space between the first electromagnet 127 and the first signal transmitting sleeve 132 along the axial direction of the rockshaft. After the first electromagnet 127 is energized, a magnetic force may be generated between the first electromagnet 127 and the first magnet 133. Therefore, by changing a magnitude and a direction of the current at the first electromagnet 127, a magnitude and a direction of the magnetic force between the first electromagnet 127 and the first magnet 133 can be changed, so that the first signal transmitting sleeve 132 drives the first signal transmitting probe 131 to slide in the first mounting cavity 121, and a distance between the first signal transmitter 130 and the first signal receiver 140 may be changed, that is, the distance between the first signal transmitter 130 and the first signal receiver 140 may be adjusted. Therefore, the accuracy of the detection result can be further ensured by adjusting different distances for multiple data collections.

Exemplarily, the first signal receiver 140 may include a first signal receiving probe 141 and a first signal receiving sleeve 142. The first signal receiving probe 141 is disposed in the first signal receiving sleeve 142, and the first signal receiving probe 141 may extend to the outside of the first signal receiving sleeve, thereby facilitating collection of data information of drilling fluid. The first signal receiving sleeve 142 is slidably disposed in the second mounting cavity 122, and a third magnet 143 is disposed at an end of the first signal receiving sleeve 142 near the bottom of the second mounting cavity 122, the third magnet 143 is disposed oppositely to the third electromagnet 128, and there is a certain space between the third electromagnet 128 and the first signal receiving sleeve 142 along the axial direction of the rockshaft. After the third electromagnet 128 is energized, a magnetic force can be generated between the third electromagnet 128 and the third magnet 143. Therefore, by changing a magnitude and a direction of the current at the third electromagnet 128, a magnitude and a direction of the magnetic force between the third electromagnet 128 and the third magnet 143 can be changed, so that the first signal receiving sleeve 142 drives the first signal receiving probe 141 to slide in the second mounting cavity 122, and a distance between the first signal receiver 140 and the first signal transmitter 130 is changed, that is, the distance between the first signal receiver 140 and the first signal transmitter 130 may be adjusted, and the accuracy of the detection result can be further ensured by adjusting different distances for multiple data collections.

Based on the above description, it may be understood that by adjusting the distance between the first electromagnet 127 and the first magnet 133, and/or the distance between the third electromagnet 128 and the third magnet 143, the distance between the first signal transmitter 130 and the first signal receiver 140 can be adjusted, that is, the collection of information of drilling fluid within different height ranges in the axial direction of the rockshaft can be realized, thereby the accuracy of the detection result can be further ensured.

Exemplarily, the first signal detector may be a laser velocimetry sensor or an ultrasonic sensor. In this embodiment, the first signal detector is an ultrasonic sensor, that is, the first signal transmitter 130 is a transmitting ultrasonic sensor and the first signal receiver 140 is a receiving ultrasonic sensor. By adopting the above structure, a velocity of drilling fluid at the corresponding position in the rockshaft can be measured, and the position of the leakage point can be judged by the change of the velocity.

In some embodiments, the first detection member 100 is further provided with a first accommodating cavity 150 and a first sealing plate, the first sealing plate is sealed at an opening of the first accommodating cavity 150, and a first circuit board is disposed in the first accommodating cavity 150, and the first circuit board is electrically connected with the first signal transmitter 130 and the first signal receiver 140 respectively, so that the data collected by the first signal detector is transmitted to the first circuit board for storage. Meanwhile, both the first electromagnet 127 and the third electromagnet 128 are electrically connected with the first circuit board, so that the first electromagnet 127 and the third electromagnet 128 may get electricity. Exemplarily, the first sealing plate may be disposed between the first accommodating cavity 150 and the first mounting seat 120, where the first sealing plate may be sealed at the opening of the first accommodating cavity 150 by a liquid high-pressure sealant, and the first sealing plate and the first mounting seat 120 may be sealed twice by fluororubber sealing tape, thereby ensuring the sealing performance in the first accommodating cavity 150, further preventing drilling fluid from entering the first accommodating cavity 150 and preventing the first circuit board from short-circuiting.

In addition, a second mounting seat 160 is further disposed on the side wall of the first detection member 100, and a first temperature detector 161 and a first pressure detector 162 are disposed on the second mounting seat 160, and both the first temperature detector 161 and the first pressure detector 162 are electrically connected with the first circuit board, so that the data collected by the first temperature detector 161 and the first pressure detector 162 is transmitted to the first circuit board for storage. Since the temperature and the pressure in the rockshaft also have a certain influence on the flow of drilling fluid, data relevant to the temperature and the pressure may be collected and calculated synchronously with the flow velocity of drilling fluid, so that the position of leakage point can be determined more accurately. Exemplarily, the first temperature detector 161 may be a temperature sensor and the first pressure detector 162 may be a pressure sensor.

Figure 6:
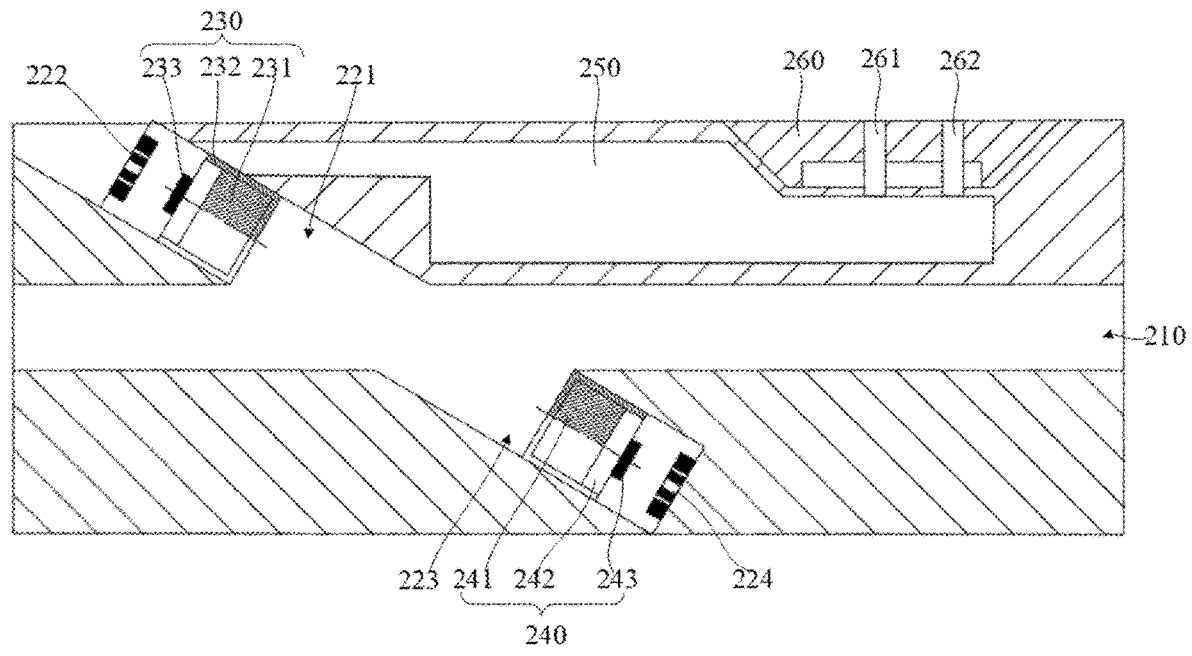
FIG. 6 is a structural schematic diagram of a second detection member provided in an embodiment of the present disclosure.

Referring to FIG. 6, the second detection member 200 may be in a columnar shape, which may be disposed side by side with the first detection member 100, that is, the side wall of the first detection member 100 is connected with a side wall of the second detection member 200; the second detection member 200 may also be disposed along the axial direction of the rockshaft with the first detection member 100, that is, the bottom end of the first detection member 100 is connected with a top end of the second detection member 200.

A fluid channel 210 penetrating through the second detection member 200 may be disposed in the second detection member 200, and the fluid channel 210 may be configured to penetrate through the second detection member 200 along the axial direction of the rockshaft, and the fluid channel 210 is in communication with the rockshaft. A second accommodating groove 220 may be further disposed in the second detection member 200, and the second accommodating groove 220 penetrates through the fluid channel 210 and intersects with a center line of the fluid channel 210; a second signal transmitter 230 and a second signal receiver 240 are disposed in the second accommodating groove 220, and the second signal transmitter 230 and the second signal receiver 240 are disposed oppositely on two sides of the fluid channel 210, and the second signal transmitter 230 transmits signals along the center line of the second accommodating groove 220, so that the second signal receiver 240 acquires data information of drilling fluid in a circumferential direction of the rockshaft.

It may be understood that the fluid channel 210 extends from a top of the second detection member 200 to a bottom of the second detection member 200 along a length direction of the second detection member 200, so that drilling fluid flows into the fluid channel 210 through the top of the second detection member 200 and flows to the outside of the fluid channel 210 through the bottom of the second detection member 200. Since the second signal transmitter 230 and the second signal receiver 240 are disposed oppositely on two sides of the fluid channel 210, so that the signal transmitted by the second signal transmitter 230 penetrates through drilling fluid in the fluid channel 210 and is received by the second signal receiver 240, thereby realizing the collection of data of drilling fluid in the circumferential direction in the fluid channel 210, that is, equivalent to realizing the collection of data information of drilling fluid in the circumferential direction of the rockshaft.

Exemplarily, the second accommodating groove 220 may include a first accommodating sub-groove 221 and a second accommodating sub-groove 223 which are disposed oppositely, that is, the first accommodating sub-groove 221 is disposed on one side of the center line of the fluid channel 210, and the second accommodating sub-groove 223 is disposed oppositely on the other side of the center line of the fluid channel 210. Meanwhile, the first accommodating sub-groove 221 and the second accommodating sub-groove 223 are each provided with an opening disposed towards the fluid channel 210, so that the first accommodating sub-groove 221 and the second accommodating sub-groove 223 are both in communication with the fluid channel 210, and drilling fluid can flow to the first accommodating sub-groove 221 and the second accommodating sub-groove 223.

In some embodiments, a second electromagnet 222 is disposed at a top of the second accommodating groove 220, that is, the second electromagnet 222 is disposed at a top of the first accommodating sub-groove 221, and a fourth electromagnet 224 is disposed at a bottom of the second accommodating groove 220, that is, the fourth electromagnet 224 is disposed at a bottom of the second accommodating sub-groove 223.

Exemplarily, the second signal transmitter 230 includes a second signal transmitting probe 231 and a second signal transmitting sleeve 232. The second signal transmitting probe 231 is disposed in the second signal transmitting sleeve 232, and the second signal transmitting probe 231 may extend to the outside of the second signal transmitting sleeve 232, thereby facilitating the collection of data information of drilling fluid. The second signal transmitting sleeve 232 is slidably disposed in the second accommodating groove 220, that is, the second signal transmitting sleeve 232 is slidably disposed in the first accommodating sub-groove 221, and a second magnet 233 is disposed at an end of the second signal transmitting sleeve 232 near the top of the second accommodating groove 220, and the second electromagnet 222 is disposed oppositely to the second magnet 233; and there is a certain space between the second electromagnet 222 and the second signal transmitting sleeve 232 in a direction along the center line of the second accommodating groove 220. After the second electromagnet 222 is energized, a magnetic force can be generated between the second electromagnet 222 and the second magnet 233. Therefore, by changing a magnitude and a direction of the current at the second electromagnet 222, a magnitude and a direction of the magnetic force between the second electromagnet 222 and the second magnet 233 can be changed, so that the second signal transmitting sleeve 232 drives the second signal transmitting probe 231 to slide in the first accommodating sub-groove 221, and the distance between the second signal transmitter 230 and the second signal receiver 240 may be changed, that is, the distance between the second signal transmitter 230 and the second signal receiver 240 may be adjusted. Therefore, the accuracy of the detection result can be further ensured by adjusting different distances for multiple data collections.

Exemplarily, the second signal receiver 240 includes a second signal receiving probe 241 and a second signal receiving sleeve 242. The second signal receiving probe 241 is disposed in the second signal receiving sleeve 242, and the second signal receiving probe 241 may extend to the outside of the second signal receiving sleeve 242, so that it is more convenient to collect data information of drilling fluid. The second signal receiving sleeve 242 is slidably disposed in the second accommodating groove 220, that is, the second signal receiving sleeve 242 is slidably disposed in the second accommodating sub-groove 223, and a fourth magnet 243 is disposed at an end of the second signal receiving sleeve 242 near the top of the second accommodating groove 220, and the fourth electromagnet 224 is disposed oppositely to the fourth magnet 243; and there is a certain space between the fourth electromagnet 224 and the second signal receiving sleeve 242 in a direction along the center line of the second accommodating groove 220. After the fourth electromagnet 224 is energized, a magnetic force can be generated between the fourth electromagnet 224 and the fourth magnet 243. Therefore, by changing a magnitude and a direction of the current at the fourth electromagnet 224, a magnitude and a direction of the magnetic force between the fourth electromagnet 224 and the fourth magnet 243 can be changed, so that the second signal receiving sleeve 242 drives the second signal receiving probe 241 to slide in the second accommodating sub-groove 223, and a distance between the second signal transmitter 230 and the second signal receiver 240 may be changed, that is, the distance between the second signal transmitter 230 and the second signal receiver 240 may be adjusted. Therefore, the accuracy of the detection result can be further ensured by adjusting different distances for multiple data collections.

Based on the above description, it may be understood that by adjusting the distance between the second electromagnet 222 and the second magnet 233, and/or the distance between the fourth electromagnet 224 and the fourth magnet 243, the distance between the second signal transmitter 230 and the second signal receiver 240 may be adjusted, that is, the collection of information of drilling fluid within different ranges in the circumferential direction of the rockshaft may be realized, thus the accuracy of the detection result can be further ensured.

In some embodiments, an angle between the center line of the second accommodating groove 220 and the center line of the fluid channel 210 is 20°-60°, for example, it may be 20°, 30°, 45° or 60°. By setting the above angles, on the premise of ensuring the collection of data information of drilling fluid in the circumferential direction of the rockshaft, it can make the second accommodating groove 220 have a long length, that is, both the first accommodating sub-groove 221 and the second accommodating sub-groove 223 have a long length, thereby increasing a movable distance of the second signal transmitter 230 in the first accommodating sub-groove 221 and a movable distance of the second signal receiver 240 in the second accommodating sub-groove 223, therefore, the adjustable distance between the second signal transmitter 230 and the second signal receiver 240 is increased, so that more data may be collected and the detection result is more accurate.

In some embodiments, the second detection member 200 is also provided with a second accommodating cavity 250 and a second sealing plate which is sealed at an opening of the second accommodating cavity 250, and a second circuit board is disposed in the second accommodating cavity 250, the second circuit board is electrically connected with the second signal transmitter 230 and the second signal receiver 240 respectively, so that the data collected by the second signal detector is transmitted to the second circuit board for storage. Meanwhile, both the second electromagnet 222 and the fourth electromagnet 224 are electrically connected with the second circuit board, so that the second electromagnet 222 and the fourth electromagnet 224 may get electricity. A second slot is disposed on an outer side wall of the second detection member 200, and the second sealing plate 250 is clamped, at both ends, to the second slot, and the second sealing plate may be sealed at the opening of the second accommodating cavity 250 by a liquid high-pressure sealant, thereby ensuring the sealing performance in the second accommodating cavity 250, further preventing drilling fluid from entering the second accommodating cavity 250 and preventing the second circuit board from short-circuiting.

In this embodiment, a third mounting seat 260 is further disposed on the side wall of the second detection member 200, and a second temperature detector 261 and a second pressure detector 262 are disposed on the third mounting seat 260, exemplarily, the second temperature detector 261 may be a temperature sensor and the second pressure detector 262 may be a pressure sensor. Both the second temperature detector 261 and the second pressure detector 262 are electrically connected with the second circuit board, so that the data collected by the second temperature detector 261 and the second pressure detector 262 is transmitted to the second circuit board for storage. Since the temperature and the pressure in the rockshaft also have a certain influence on the flow of drilling fluid, data relevant to the temperature and the pressure may be collected and calculated synchronously with the flow velocity of the drilling fluid, so that the position of leakage point can be determined more accurately.

In some embodiments, a telescopic device 300 and a first centralizer 400 are disposed between the first detection member 100 and the second detection member 200. The telescopic device 300 is connected, at one end, with the first detection member 100, exemplarily, the telescopic device 300 may be connected with the first detection member 100 by welding; the telescopic device 300 is connected, at the other end, with the second detection member 200 through the first centralizer 400, and a telescopic direction of the telescopic device 300 is parallel to the axial direction of the rockshaft; moreover, the first centralizer 400 is provided with a liquid inlet hole 410, which is configurable to be in communication with the rockshaft and the fluid channel 210, so that drilling fluid may flow into the fluid channel 210 through the liquid inlet hole 410.

Exemplarily, the liquid inlet hole 410 may be an obround hole, and the liquid inlet hole 410 may be plural, and a plurality of liquid inlet holes 410 are uniformly disposed around the outer periphery of the first centralizer 400, so that drilling fluid flows around the outer periphery of the first centralizer 400 into the fluid channel 210, thereby more accurately collecting data information of drilling fluid distributed along the circumferential direction of the rockshaft, and further improving the accuracy of the detection result.

Figure 7:
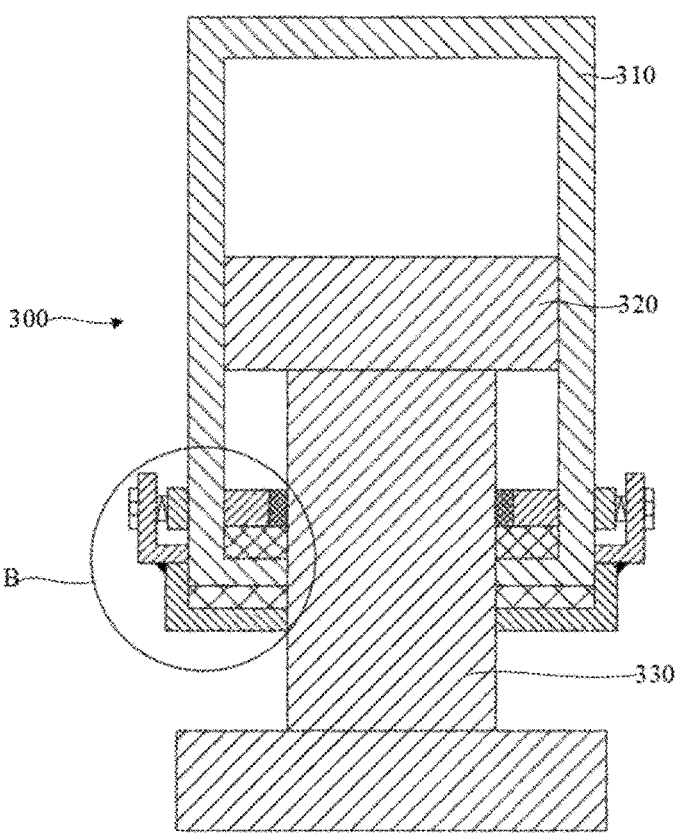
FIG. 7 is a structural schematic diagram of a telescopic device provided in an embodiment of the present disclosure.
Figure 8:
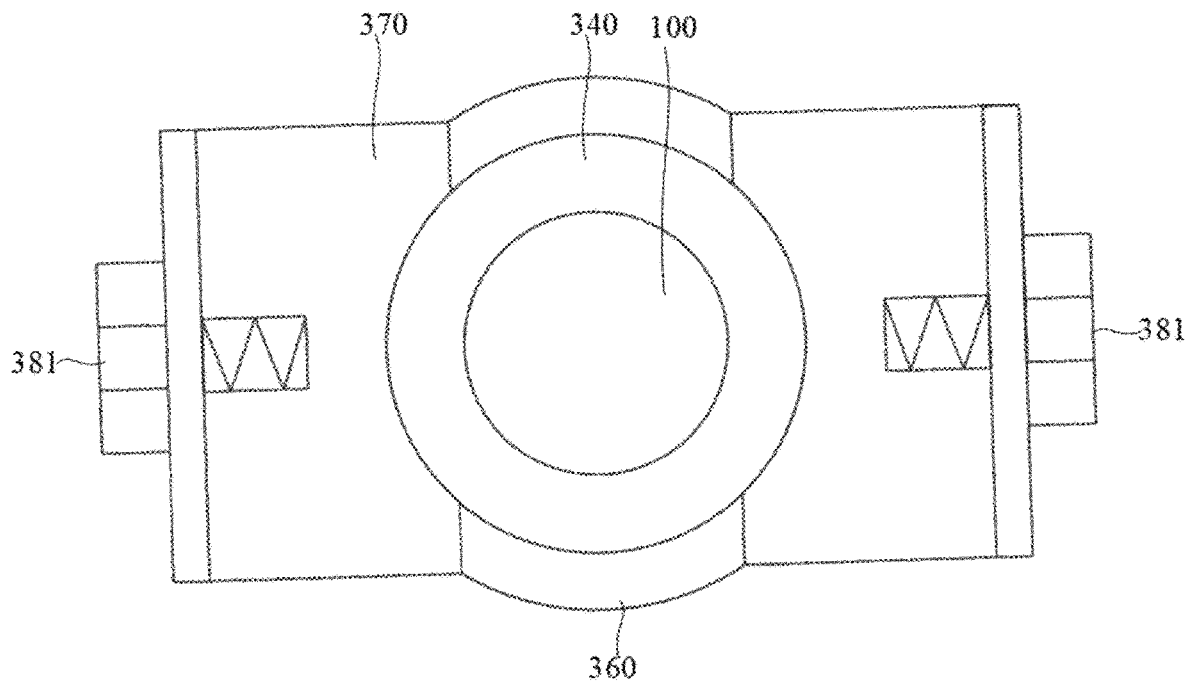
FIG. 8 is a top view of a telescopic device provided in an embodiment of the present disclosure.
Figure 9:
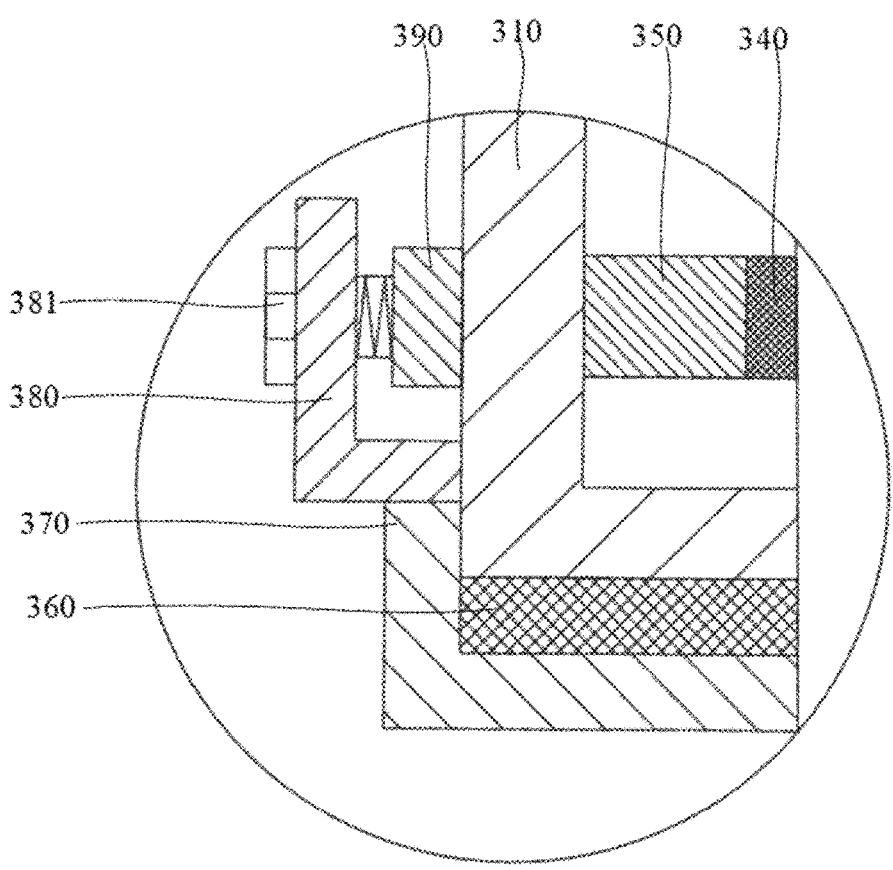
FIG. 9 is a partial structural schematic diagram of an area B of the telescopic device in FIG. 7 provided in an embodiment of the present disclosure.

As shown in FIG. 7 to FIG. 9, the telescopic device includes a cylinder body, a piston and a telescopic rod, and the cylinder body is firmly connected with the first detection member; the piston is slidably disposed in the cylinder body, and an outer side wall of the piston fits an inner side wall of the cylinder body; one end of the telescopic rod is firmly connected with the piston, and the other end thereof is connected with the second detection member. Exemplarily, the telescopic device may be a hydraulic telescopic cylinder or an air cylinder, etc., and the hydraulic telescopic cylinder is described as an example in the following.

In this embodiment, a cavity is formed in the cylinder body 310, the piston 320 fits an inner wall of the cavity, a space between the piston 320 and a top of the cavity forms an oil inlet cavity, and a space between the piston 320 and a bottom of the cavity forms an oil return cavity. An opening is disposed on one side of the cavity; one end of the telescopic rod 330 is slidably disposed in the cylinder body 310 and firmly connected with the piston 320 of which the outer peripheral surface fits an inner wall surface of the cylinder body 310, and the other end of the telescopic rod 330 extends to the outside of the cylinder body 310 through the opening, and this end is provided with a first seal and a second seal, and the opening is sealed by the first seal and the second seal.

Exemplarily, the first seal may be disposed in the cylinder body 310, the first seal may include a first sealing gasket 340 and a first limit plate 350, the first sealing gasket 340 and the first limit plate 350 may be made of a rubber material, and the first sealing gasket 340 and the first limit plate 350 may be in an annular shape. The first sealing gasket 340 fits the outer periphery of the telescopic rod 330, and the first limit plate 350 is disposed around the outer periphery of the first sealing gasket 340, and an inner wall of the first limit plate 350 fits the first sealing gasket 340, and an outer wall of the first limit plate 350 is connected with the inner wall of the cylinder body 310. Therefore, by adopting the above structure, the first sealing gasket 340 can seal a gap between the telescopic rod 330 and the cylinder body 310, thereby preventing dust from entering the cylinder body 310, and further preventing the normal use of the telescopic device 300 from being affected by excessive accumulation of dust in the cylinder body 310. Meanwhile, when the telescopic rod 330 expands and contracts, the first sealing gasket 340 may be effectively limited and fixed through the cooperation between the cylinder body 310 and the first limit plate 350, so as to avoid its dislocated movement.

Exemplarily, the second seal may be disposed outside the cylinder body 310, and it may include a second sealing gasket 360 and a second limit plate 370, both the second sealing gasket 360 and the second limit plate 370 may be made of a rubber material, and both the second sealing gasket 360 and the second limit plate 370 may be in an annular shape. The second sealing gasket 360 is sleeved on the outer periphery of the telescopic rod 330, and an inner peripheral surface of the second sealing gasket 360 fits an outer peripheral surface of the telescopic rod 330, and the second sealing gasket 360 abuts against a bottom end surface of the cylinder body 310. The second limit plate 370 is sleeved on the outer periphery of the telescopic rod 330, and an upper end face of the second limit plate 370 is provided with a concave part, and the structure of the concave part is matched with that of the second sealing gasket 360, so that the second sealing gasket 360 can be disposed at the concave part, and the bottom end of the cylinder body 310 is clamped in the concave part; in addition, both side surfaces of the second limit plate 370 are connected to the cylinder body 310 through auxiliary fixing members. By adopting the above structure, the second sealing gasket 360 can seal the gap between the telescopic rod 330 and the cylinder body 310, thereby further preventing dust from entering the cylinder body 310, and further preventing the normal use of the telescopic device 300 from being affected by excessive accumulation of dust in the cylinder body 310. Meanwhile, when the telescopic rod 330 expands and contracts, the second sealing gasket 360 may be effectively limited and fixed through the cooperation between the cylinder body 310 and the second limit plate 370, so as to avoid its dislocated movement.

Exemplarily, the auxiliary fixing member may include a fixing plate 380, a fixing block 390 and a securing bolt 381.

The fixing plate 380 may be in an L-shape, one end of the fixing plate 380 is detachably connected with an outer side wall of the cylinder body 310, and the other end of the fixing plate 380 is disposed in parallel with the cylinder body 310 with a gap therebetween, and the fixing plate 380 is provided with a first threaded hole running therethrough at this end of the fixing plate 380. In addition, the fixing block 390 is located in the gap between the fixing plate 380 and the cylinder body 310, and is firmly connected with the side wall of the cylinder body 310. The fixing block 390 is provided with a second threaded hole which is disposed oppositely to the first threaded hole, the securing bolt 381 sequentially passes through the first threaded hole and the second threaded hole, and the fixing plate 380 is firmly connected with the fixing block 390, so that a detachable connection is achieved between the fixing plate 380 and the cylinder body 310. Therefore, by adopting the above structure, when the second sealing gasket 360 is damaged, the second limit plate 370 and the cylinder body 310 may be separated by unscrewing the securing bolt 381, for replacement of the second sealing gasket 360.

In some embodiments, the lost circulation detection device further includes a connector 600, and the connector 600 may be in a columnar shape. The connector 600 is disposed along the axial direction of the rockshaft and is connected with the bottom of the second detection member 200, and a protective cover 700 is further disposed at a bottom of the connector 600. By arranging the connector 600 and the protective cover 700, it is possible to avoid damages to internal parts of the lost circulation detection device when the device hits other objects in the rockshaft during detection.

In addition, the connector 600 and the second detection member 200 are connected through a second centralizer 500, that is, one end of the second centralizer 500 is sleeved on a top of the connector 600 and the other end thereof is sleeved on the bottom of the second detection member 200. The second centralizer 500 is provided with a liquid outlet hole 510 which is configurable to be in communication with the rockshaft and the fluid channel 210 respectively, so that drilling fluid may flow out of the fluid channel 210 into the rockshaft through the liquid outlet hole 510.

Exemplarily, the liquid outlet hole 510 may be an obround hole, and the liquid outlet hole 510 may be plural, and a plurality of liquid outlet holes 510 are uniformly disposed around the outer periphery of the first centralizer 400, so that drilling fluid flows around the outer periphery of the first centralizer 400 into the fluid channel 210, thereby more accurately collecting data information of drilling fluid distributed along the circumference direction of the rockshaft, and further improving the accuracy of the detection result.

Based on the above description, by arranging the first detection member 100 and the second detection member 200, where the first detection member 100 is provided with the first signal transmitter 130 and the first signal receiver 140 which are disposed oppositely along the axial direction of the rockshaft, the collection of data information of drilling fluid in the axial direction of the rockshaft is realized; meanwhile, the fluid channel 210 penetrating through the second detection member 200 is disposed in the second detection member 200, and the fluid channel 210 is in communication with the rockshaft, so that drilling fluid can flow into the fluid channel 210; where the second detection member 200 is provided with a second signal transmitter 230 and a second signal receiver 240 that penetrate through the fluid channel 210 and are disposed oppositely, the collection of data information of drilling fluid in the circumferential direction of the rockshaft is achieved. Therefore, when positions of the leakage detected by the first detection member 100 and the second detection member 200 are in the same range, it indicates that the position of the leakage point is relatively accurate; when the positions of the leakage detected by the first detection member 100 and the second detection member 200 are in different ranges, it indicates that there is an error in the collected data, so that the staff can be reminded to find the problem in time and make corresponding adjustments. Therefore, by using the above two detection members for mutual calibration of the position of a leakage, the detection result is more accurate and the positioning accuracy is higher, which solves the technical problem that the lost circulation detection device in the related art cannot accurately determine the position of the leakage point.

In the description of the embodiments of the present disclosure, it is to be understood that orientations or positional relationships indicated by terms "center", "longitudinal", "lateral", "length" "width", "thickness", "upper", "lower", "front", "rear", "left", "right", "vertical", "horizontal", "top", "bottom", "inner", "outer", "clockwise", "counterclockwise", "axial direction", "radial direction", "circumferential direction", etc. are based on orientations or positional relationships shown in the drawings, and are only intended to facilitate describing the embodiments of the present disclosure and simplifying the description, and not to indicate or imply that the indicated device or element must have a particular orientation, be constructed or operated in a particular orientation, and therefore they cannot be understood as a limitation to the embodiments of the present disclosure.

In addition, terms "first" and "second" are used only for descriptive purposes and cannot be understood to indicate or imply relative importance or imply the number of technical features indicated. Therefore, features defined with "first" or "second" or "third" may explicitly or implicitly include at least one of the features. In the description of the embodiments of the present disclosure, "a plurality of" means at least two, such as two, three, etc., unless otherwise clearly and specifically defined.

In the embodiments of the present disclosure, unless otherwise clearly specified and defined, terms "mounting", "connection", "connecting", "fixing" and the like should be understood in a broad sense, for example, it may be a fixed connection, may be a detachable connection, or may be integrated connection; it may be a mechanical connection, and may be also an electrical connection; it may be a direct connection, or an indirect connection through an intermediate medium, or communication within two elements or interaction between two elements. For those ordinarily skilled in the art, the specific meanings of the above terms in the embodiments of the present disclosure may be understood according to the specific situation.

In the embodiments of the present disclosure, unless otherwise clearly specified and defined, a first feature being "above" or "below" a second feature may include the first feature being in direct contact with the second feature, or may include the first feature being in indirect contact with the second feature through an intermediate medium. Moreover, the first feature being "over", "above" and "on" the second feature includes the first feature being directly above and diagonally above the second feature, or simply indicates that a horizontal height of the first feature is higher than that of the second feature. The first feature being "under", "below" and "beneath" the second feature may be that the first feature is directly below and diagonally below the second feature, or simply indicates that the horizontal height of the first feature is lower than that of the second feature.

In the description of this specification, descriptions with reference to terms "an embodiment", "some embodiments", "an example", "a specific example" or "some examples" mean that specific features, structures, materials or characteristics described in connection with this embodiment or example are included in at least one embodiment or example of the embodiments of the present disclosure. In this specification, the schematic expressions of the above terms are not necessarily aimed at the same embodiment or example. Moreover, the specific features, structures, materials or characteristics described may be combined in any one or more embodiments or examples in a suitable manner. In addition, those skilled in the art can incorporate and combine different embodiments or examples and features of different embodiments or examples described in this specification without contradictions.

Although the embodiments of the present disclosure have been shown and described above, it may be understood that the above embodiments are exemplary and cannot be understood as a limitation of the embodiments of the present disclosure, and those ordinarily skilled in the art can make changes, modifications, substitutions and variations to the above embodiments within the scope the embodiments of the present disclosure.

What is claimed is:

1. A lost circulation detection device, comprising:
a first detection member, wherein a first accommodating groove is disposed on a side wall of the first detection member, and the first accommodating groove is configurable to be in communication with a rockshaft; a first signal transmitter and a first signal receiver are disposed in the first accommodating groove, and the first signal transmitter and the first signal receiver are disposed oppositely and spaced apart along an axial direction of the rockshaft, and the first signal transmitter transmits a signal along the axial direction of the rockshaft, so that the first signal receiver acquires data information of drilling fluid in the axial direction of the rockshaft; and
a second detection member securely connected with the first detection member; wherein a fluid channel penetrating through the second detection member is disposed in the second detection member, and the fluid channel is configurable to be in communication with the rockshaft; a second accommodating groove is further disposed in the second detection member, and the second accommodating groove penetrates through the fluid channel and intersects with a center line of the fluid channel; a second signal transmitter and a second signal receiver are disposed in the second accommodating groove, and the second signal transmitter and the second signal receiver are disposed oppositely on two sides of the fluid channel, and the second signal transmitter transmits a signal along a center line of the second accommodating groove, so that the second signal receiver acquires data information of drilling fluid in a circumferential direction of the rockshaft.

2. The lost circulation detection device according to claim 1, wherein a first mounting seat is disposed in the first accommodating groove, and a first mounting cavity and a second mounting cavity are disposed oppositely and spaced apart on the first mounting seat along the axial direction of the rockshaft, and the first signal transmitter is disposed in the first mounting cavity, and the first signal receiver is disposed in the second mounting cavity, and a transmitting end of the first signal transmitter is disposed oppositely to and collinear with a receiving end of the first signal receiver.

3. The lost circulation detection device according to claim 2,
wherein the first signal transmitter comprises a first signal transmitting probe and a first signal transmitting sleeve, the first signal transmitting probe is disposed in the first signal transmitting sleeve; the first signal transmitting sleeve is slidably disposed in the first mounting cavity, and a first magnet is disposed at an end of the first signal transmitting sleeve near a top of the first mounting cavity; and
a first electromagnet is disposed at the top of the first mounting cavity, and the first electromagnet is disposed oppositely to the first magnet; and along the axial direction of the rockshaft, there is a certain space between the first electromagnet and the first signal transmitting sleeve.

4. The lost circulation detection device according to claim 3,
wherein the second signal transmitter comprises a second signal transmitting probe and a second signal transmitting sleeve, and the second signal transmitting probe is disposed in the second signal transmitting sleeve; the second signal transmitting sleeve is slidably disposed in the second accommodating groove, and a second magnet is disposed at an end of the second signal transmitting sleeve near a top of the second accommodating groove; and
a second electromagnet is disposed at the top of the second accommodating groove, and the second electromagnet is disposed oppositely to the second magnet; and in a direction along the center line of the second accommodating groove, there is a certain space between the second electromagnet and the second signal transmitting sleeve.

5. The lost circulation detection device according to claim 4, wherein an angle between the center line of the second accommodating groove and the center line of the fluid channel is 20°-60°.

6. The lost circulation detection device according to claim 3, wherein the first detection member and the second detection member are disposed along the axial direction of the rockshaft, and a telescopic device is disposed between the first detection member and the second detection member, and a telescopic direction of the telescopic device is parallel to the axial direction of the rockshaft; and the telescopic device is connected, at one end, with the first detection member, and the telescopic device is connected, at the other end, with the second detection member through a first centralizer, and the first centralizer is provided with a liquid inlet hole which is configurable to be in communication with the rockshaft and the fluid channel respectively.

7. The lost circulation detection device according to claim 6, wherein the telescopic device comprises:

a cylinder body firmly connected with the first detection member;

a piston slidably disposed in the cylinder body, wherein an outer side wall of the piston fits an inner side wall of the cylinder body; and a telescopic rod, one end of which is firmly connected with the piston, and the other end of which is connected with the second detection member.

8. The lost circulation detection device according to claim 3, wherein a protector for protecting the second detection member is disposed at a bottom of the second detection member.

9. The lost circulation detection device according to claim 2, wherein the second signal transmitter comprises a second signal transmitting probe and a second signal transmitting sleeve, and the second signal transmitting probe is disposed in the second signal transmitting sleeve; the second signal transmitting sleeve is slidably disposed in the second accommodating groove, and a second magnet is disposed at an end of the second signal transmitting sleeve near a top of the second accommodating groove; and a second electromagnet is disposed at the top of the second accommodating groove, and the second electromagnet is disposed oppositely to the second magnet; and in a direction along the center line of the second accommodating groove, there is a certain space between the second electromagnet and the second signal transmitting sleeve.

10. The lost circulation detection device according to claim 9, wherein an angle between the center line of the second accommodating groove and the center line of the fluid channel is 20°-60°.

11. The lost circulation detection device according to claim 2, wherein the first detection member and the second detection member are disposed along the axial direction of the rockshaft, and a telescopic device is disposed between the first detection member and the second detection member, and a telescopic direction of the telescopic device is parallel to the axial direction of the rockshaft; and the telescopic device is connected, at one end, with the first detection member, and the telescopic device is connected, at the other end, with the second detection member through a first centralizer, and the first centralizer is provided with a liquid inlet hole which is configurable to be in communication with the rockshaft and the fluid channel respectively.

12. The lost circulation detection device according to claim 11, wherein the telescopic device comprises:

a cylinder body firmly connected with the first detection member;

a piston slidably disposed in the cylinder body, wherein an outer side wall of the piston fits an inner side wall of the cylinder body; and a telescopic rod, one end of which is firmly connected with the piston, and the other end of which is connected with the second detection member.

13. The lost circulation detection device according to claim 2, wherein a protector for protecting the second detection member is disposed at a bottom of the second detection member.

14. The lost circulation detection device according to claim 1, wherein the second signal transmitter comprises a second signal transmitting probe and a second signal transmitting sleeve, and the second signal transmitting probe is disposed in the second signal transmitting sleeve; the second signal transmitting sleeve is slidably disposed in the second accommodating groove, and a second magnet is disposed at an end of the second signal transmitting sleeve near a top of the second accommodating groove; and a second electromagnet is disposed at the top of the second accommodating groove, and the second electromagnet is disposed oppositely to the second magnet; and in a direction along the center line of the second accommodating groove, there is a certain space between the second electromagnet and the second signal transmitting sleeve.

15. The lost circulation detection device according to claim 14, wherein an angle between the center line of the second accommodating groove and the center line of the fluid channel is 20°-60°.

16. The lost circulation detection device according to claim 1, wherein the first detection member is provided with a first accommodating cavity and a first sealing plate, and the first sealing plate seals an opening of the first accommodating cavity; and a first circuit board is disposed in the first accommodating cavity, and the first circuit board is electrically connected with the first signal transmitter and the first signal receiver, respectively; and the second detection member is provided with a second accommodating cavity and a second sealing plate, and the second sealing plate seals an opening of the second accommodating cavity; a second circuit board is disposed in the second accommodating cavity, and the second circuit board is electrically connected with the second signal transmitter and the second signal receiver, respectively.

17. The lost circulation detection device according to claim 16, wherein a first temperature detector and a first pressure detector are disposed on the side wall of the first detection member, and both the first temperature detector and the first pressure detector are electrically connected with the first circuit board; and a second temperature detector and a second pressure detector are disposed on a side wall of the second detection member, and both the second temperature detector and the second pressure detector are electrically connected with the second circuit board.

18. The lost circulation detection device according to claim 1, wherein the first detection member and the second detection member are disposed along the axial direction of the rockshaft, and a telescopic device is disposed between the first detection member and the second detection member, and a telescopic direction of the telescopic device is parallel to the axial direction of the rockshaft; and the telescopic device is connected, at one end, with the first detection member, and the telescopic device is connected, at the other end, with the second detection member through a first centralizer, and the first centralizer is provided with a liquid inlet hole which is configurable to be in communication with the rockshaft and the fluid channel respectively.

19. The lost circulation detection device according to claim 18, wherein the telescopic device comprises:

a cylinder body firmly connected with the first detection member;

a piston slidably disposed in the cylinder body, wherein an outer side wall of the piston fits an inner side wall of the cylinder body; and a telescopic rod, one end of which is firmly connected with the piston, and the other end of which is connected with the second detection member.

20. The lost circulation detection device according to claim 1, wherein a protector for protecting the second detection member is disposed at a bottom of the second detection member.

\* \* \* \* \*